United States Patent [19]

Niznick

[11] Patent Number: 4,758,161
[45] Date of Patent: Jul. 19, 1988

[54] COPING INSERT FOR USE WITH A DENTAL IMPLANT

[75] Inventor: Gerald A. Niznick, Encino, Calif.

[73] Assignee: Core-Vent Corporation, Encino, Calif.

[21] Appl. No.: 8,183

[22] Filed: Jan. 28, 1987

[51] Int. Cl.[4] .............................................. A61C 8/00
[52] U.S. Cl. .................................. 433/173; 433/201.1
[58] Field of Search ............... 433/173, 174, 175, 176, 433/201

[56] References Cited

U.S. PATENT DOCUMENTS

| | | | |
|---|---|---|---|
| 711,324 | 10/1902 | Lacy | 433/173 |
| 866,304 | 9/1907 | Roach | 433/177 |
| 2,112,007 | 9/1932 | Adams | 433/174 |
| 2,347,567 | 3/1938 | Kresse | 424/81 |
| 2,609,604 | 4/1944 | Sprague | 433/174 |
| 2,774,141 | 12/1956 | Quinn | 433/213 |
| 3,435,526 | 4/1969 | Brancato | 433/174 |
| 3,499,222 | 3/1970 | Linkow et al. | 433/174 |
| 3,732,621 | 5/1973 | Bostrom | 433/174 |
| 3,787,975 | 1/1974 | Zuest | 433/182 |
| 3,849,888 | 11/1974 | Linkow | 433/176 |
| 4,016,651 | 4/1977 | Kawahara et al. | 433/174 |
| 4,053,982 | 10/1977 | Weissman | 433/225 |
| 4,109,383 | 8/1978 | Reed et al. | 433/72 |
| 4,177,562 | 12/1979 | Miller | 433/174 |
| 4,180,910 | 1/1980 | Straumann | 433/173 |
| 4,187,609 | 2/1980 | Edelman | 433/176 |
| 4,195,367 | 4/1980 | Kraus | 623/18 |
| 4,204,321 | 5/1980 | Scott | 433/177 |
| 4,259,072 | 3/1981 | Hirabayashi et al. | 433/173 |
| 4,290,755 | 9/1981 | Scott | 433/173 |
| 4,302,188 | 11/1981 | Driskell | 433/173 |
| 4,334,865 | 6/1982 | Borle | 433/221 |
| 4,359,318 | 11/1982 | Gittleman | 433/173 |
| 4,416,629 | 11/1983 | Mozsary et al. | 433/174 |
| 4,431,416 | 12/1984 | Niznick | 433/174 |
| 4,468,200 | 8/1984 | Munch | 433/174 |
| 4,488,875 | 2/1984 | Niznick | 433/173 |
| 4,552,532 | 11/1985 | Mozsary | 433/173 |
| 4,573,922 | 3/1986 | Bello | 433/176 |
| 4,645,453 | 2/1987 | Niznick | 433/173 |
| 4,668,191 | 5/1987 | Plischka | 433/174 |

FOREIGN PATENT DOCUMENTS

| | | |
|---|---|---|
| 73177 | 3/1983 | European Pat. Off. . |
| 2834890 | 5/1979 | Fed. Rep. of Germany . |
| 3027138 | 7/1980 | Fed. Rep. of Germany . |
| 3423752 | 10/1985 | Fed. Rep. of Germany . |
| 98988 | 1/1973 | Japan . |
| 42665 | 10/1976 | Japan . |
| 83591 | 1/1977 | Japan . |
| 6141580 | 9/1986 | Japan . |
| 8601705 | 3/1986 | PCT Int'l Appl. . |
| 604674 | 9/1978 | Switzerland . |
| 1203093 | 8/1970 | United Kingdom . |
| 1291470 | 10/1972 | United Kingdom . |
| 1352188 | 5/1974 | United Kingdom . |
| 1544784 | 4/1979 | United Kingdom . |

OTHER PUBLICATIONS

Promotional literature for Zest Anchor.
Promotional literature for Scodenco O-SO Attachment System.
The Journal of Prosthetic Dentistry, vol. 50, No. 1, published by the C. V. Mosby Company in Jul., 1983.
Implant Prosthodontics, published by Core-Vent Corporation.
Osseointegrated Titanium Implants by T. Albrektsson et al, Acta orthop. scand. 52, 155–170, 1981, pp. 167–168.
Osseointegrated Implants in the Treatment of the Edentulous Jaw, by P-I Branemark et al, 1977, pp. 24, 25, 29, 31, and 109.

Primary Examiner—Robert Peshock
Attorney, Agent, or Firm—Kendrick, Lorig & Bright

[57] ABSTRACT

A thermoplastic, one-piece coping insert adapted for use with a dental implant anchoring means includes a shaft that fits into an opening in a dental implant, an abutment head joined to the shaft and adapted to conform to, and fit smoothly on, or in the top surface of the dental implant, a bendable restriction or groove to facilitate preferential bending of the insert at the restriction when the insert is heated to the softening temperature of a thermoplastic, and a relatively unbendable post atop the restriction for receiving and supporting a dental prosthesis such as one or more prosthetic teeth.

13 Claims, 4 Drawing Sheets

COPING INSERT FOR USE WITH A DENTAL IMPLANT

This invention relates to a coping insert, preferably a one-piece coping insert, and preferably a thermoplastic coping insert, adapted for insertion into a dental implant anchoring means. The insert comprises shaft means adapted for insertion into shaft-receiving means in a dental implant anchoring means. The shaft means can be of substantially uniform diameter along its entire length, or can have two or more sections of different diameters to fit into implants with shafts having sections of corresponding dimensions.

Atop, and joined to the shaft means, is abutment head means. The abutment head means is preferably of a size and shape to conform to, or complement or fit flushly with the abutting surface of a dental implant anchoring means when the shaft of the coping insert is inserted into the implant. The abutment head means can have a cylindrical cross-section, or a frustoconical cross-section, tapering upwardly and outwardly from the base of the abutment head means where the abutment head means joins to the shaft means.

Joined to and atop the abutment head means, in preferred embodiments, is a preferentially bendable restriction means that is integral with the insert. The restriction means links the abutment head means to means for joining the insert means to, and supporting dental prosthesis means such as a tooth or a bridge. The dental prosthesis-engaging and supporting means is, in preferred embodiments, a frustoconical post that can, in some embodiments, taper inwardly and upwardly from the restriction means. The restriction means is of sufficient size and shape to bend preferentially when the insert is thermoplastic, and is heated to the softening temperature of the thermoplastic from which the insert is made.

In preferred embodiments, the shaft means can include one or more partially or completely circumferential grooves or score lines to facilitate severing a portion from the shaft means to shorten its length. Similarly, the dental prosthesis engaging means atop the restriction means can include one or more partially or completely circumferential grooves or score lines to facilitate severing and removing a portion of the prosthesis engaging means, preferably in a plane perpendicular to the longitudinal axis of the dental prosthesis engaging means. The dental prosthesis engaging/supporting means can also include one or more flattened side areas to prevent a prosthesis mounted thereon from moving, as, for example, by rotation, from its desired position.

The invention can better be understood by reference to the drawings in which.

Figure 1:
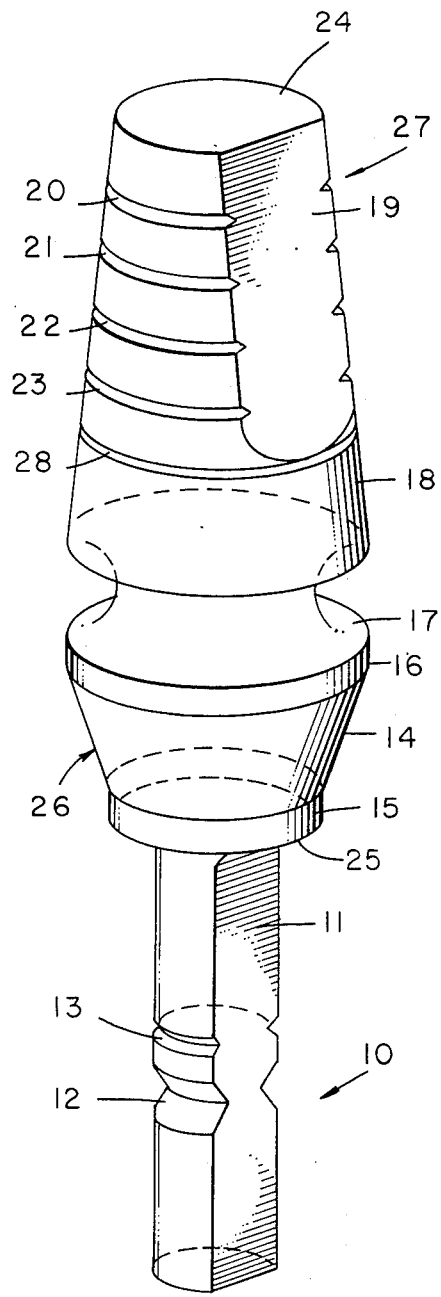
FIG. 1 is a perspective view of a first embodiment of the coping insert of this invention.

FIG. 1 shows a one-piece, thermoplastic coping insert, generally designated 10, including shaft 11 adapted for insertion into a passage inside a dental implant anchoring means. Circumferential grooves 12 and 13 facilitate severing a portion of shaft 11 to shorten its length, as necessary, to fit within the shaft-receiving passage in the dental implant anchoring means. Joined to and atop shaft 11 is abutment head portion 26 that includes planar bottom surface 25, cylindrical-shaped portion 15 contiguous with the edge of botto surface 25 and conical surface 14 slanting upwardly and outwardly from surface 25. Contiguous with conical surface 14 is cylindrical-shaped surface 16.

Restriction 17 is of a size and shape, here with a rounded, concave profile, to facilitate preferential bending at restriction 17 when insert 10 is heated to the softening temperature of the thermoplastic material from which insert 10 is made. At the softening temperature of thermoplastic insert 10, post portion 27 can be moved to a desired angle or attitude, but will not itself bend or distort. After insert 10 cools to a temperature below the softening point of the thermoplastic, post 27 remains at the desired angle or attitude. Since insert 10 is made from a thermoplastic such as acrylic, the insert can be reheated, and post 27 moved repeatedly as desired or as necessary.

Post 27 atop restriction 17 is frustoconical in shape and includes a flat upper surface 24 and a conical sidewall 18. Conical sidewall 18 can include one or more flat planar areas 19, which restrain rotation of a dental prosthesis joined to post 27. Score lines 20, 21, 22, 23 and 28 facilitate severing portions of post means 27, as necessary, in planes parallel to surface 24, to accommodate dental prostheses of varying sizes and shapes.

Figure 2:
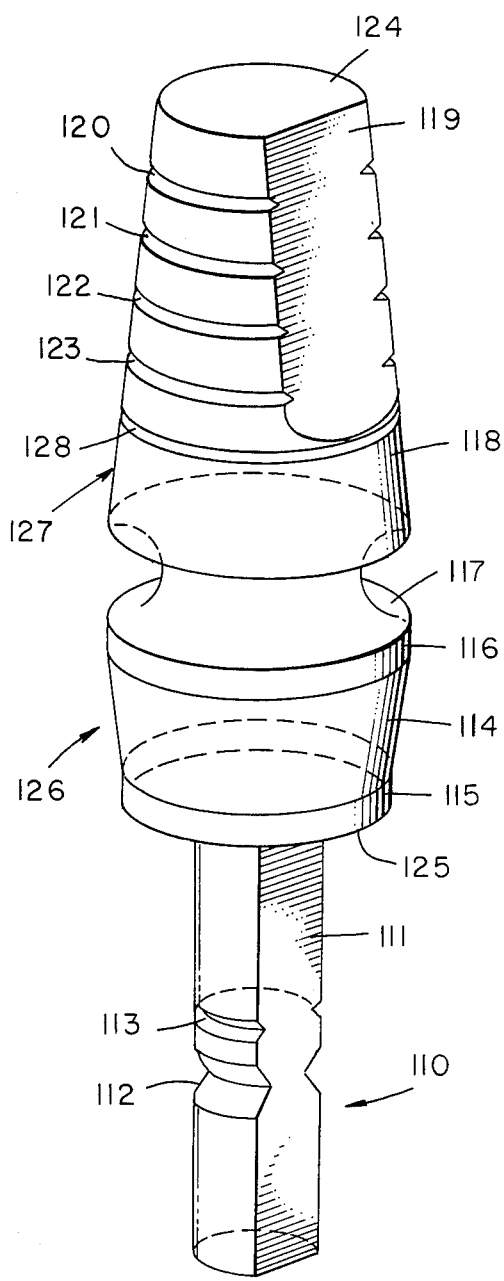
FIG. 2 is a perspective view of a second embodiment of the coping insert of this invention.
Figure 3:
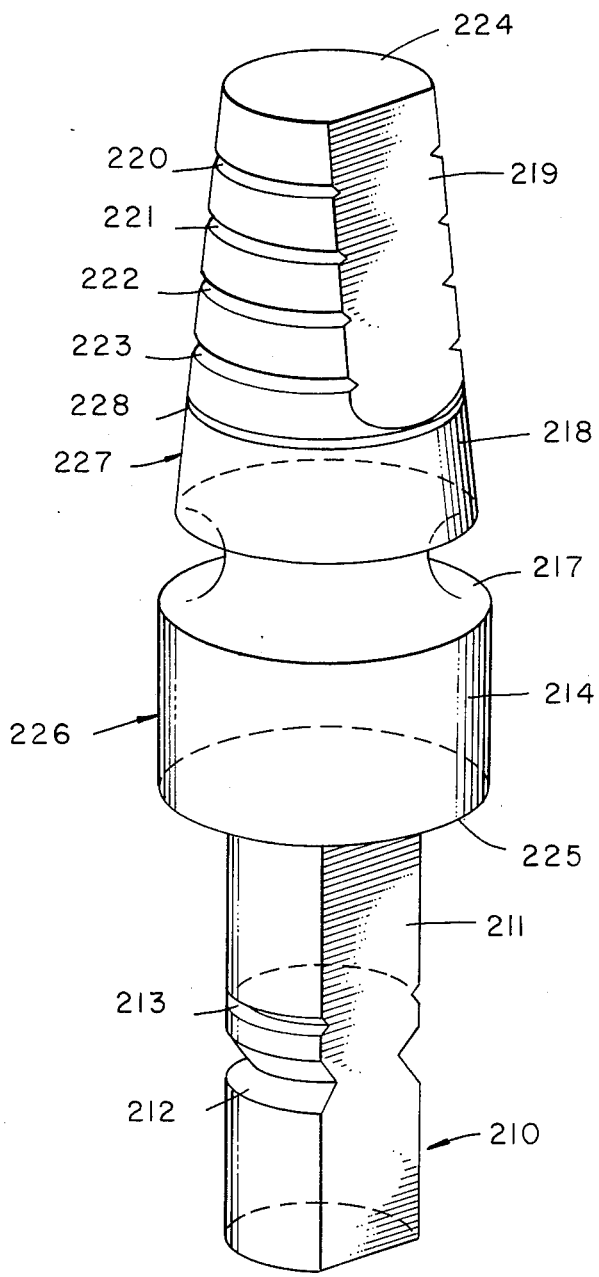
FIG. 3 is a perspective view of a third embodiment of the coping insert of this invention.

FIGS. 2 and 3 show second and third embodiments, respectively, of the thermoplastic coping insert shown in FIG. 1. The embodiment shown in FIG. 2 is identical to that shown in FIG. 1, except that abutment head means 126 has a sidewall 114 that tapers upwardly and outwardly (with respect to base 125), but at a much smaller angle than sidewall 14 (with respect to base 25) in the embodiment shown in FIG. 1. All other numbered parts of the second embodiment (FIG. 2) are the same as those in the first embodiment (FIG. 1). However, the numbers in FIG. 2 are 100 units higher than the corresponding parts in FIG. 2. For example, part 111 in FIG. 2 is the same as part 11 in FIG. 1.

The third embodiment shown in FIG. 3 is identical to the first embodiment shown in FIG. 1, except that the abutment head 214 has a substantially cylindrical cross-section, and does not taper outwardly and upwardly from its base 225. All other numbered parts of the third embodiment (FIG. 3) are the same as those in the first embodiment (FIG. 1), except that the numbers in FIG. 3 are 200 units higher than the corresponding parts in FIG. 1. For example, part 211 in FIG. 3 is the same as part 11 in FIG. 1.

Figure 4:
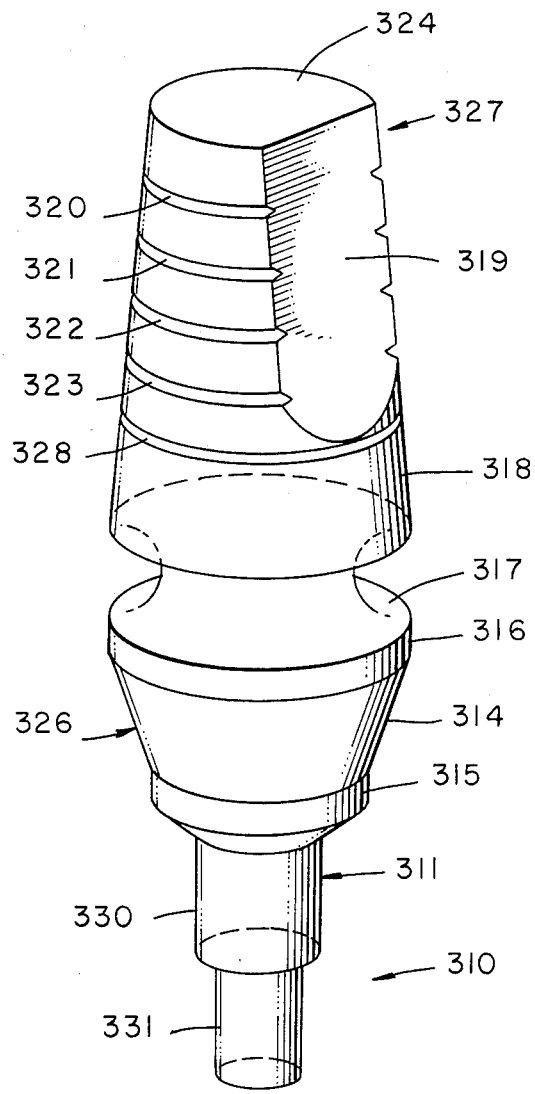
FIG. 4 is a perspective view of a fourth embodiment of the coping insert of this invention.

The fourth embodiment shown in FIG. 4 is identical to the first embodiment shown in FIG. 1, except that shaft 311 has two portions 330 and 331 that differ from one another in diameter to complement, and fit within a passage inside a dental implant anchoring means having two regions of complementary diameters. All of the numbered parts of the fourth embodiment (FIG. 4) are the same as those in the first embodiment (FIG. 1), except that the numbers in FIG. 4 are 300 units higher than the corresponding parts in FIG. 1. For example, part 311 in FIG. 4 is the same as part 11 in FIG. 1.

Figure 5:
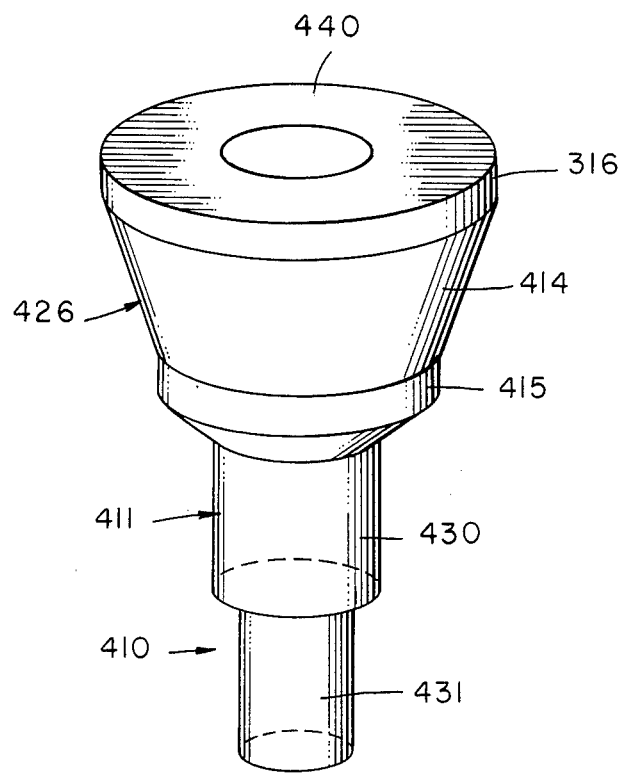
FIG. 5 is a perspective view of a fifth embodiment of the coping insert of this invention.

The fifth embodiment shown in FIG. 5 is identical to the fourth embodiment shown in FIG. 4, except that abutment head 414 has a substantially planar upper surface 440. Substantially planar surface 440 is adapted to receive a screw or other casting support that can be inserted in a hole formed by drilling or otherwise into substantially planar surface 440. A dental prosthesis can then be cast around this insert, and the abutment head 414 can be molded or otherwise shaped to complement and accommodate a desired dental prosthesis joined to such a prosthesis-supporting member. All of the numbered parts of this fifth embodiment (FIG. 5) are the same as those in the fourth embodiment (FIG. 4), except that the numbers in FIG. 5 are 100 units higher than the corresponding parts in FIG. 4. For example, part 414 in FIG. 5 is the same as part 314 in FIG. 4.

The new thermoplastic coping inserts have several advantages. These inserts have no undercut portion above the shaft, and fit flushly with the top of the dental implant anchoring means that they are adapted to be inserted into. These inserts can be bent and rebent repeatedly to any desired angle without distorting the abutment head, or post, and the post can be cut and shaped as desired to form a pattern for fabrication of a cast metal post to receive and support prostheses of substantially virtually all sizes and shapes, such as crowns designed to extend under gum tissue. Moreover, these inserts can be used in either direct or indirect methods for molding dental prostheses.

In the direct molding of dental prostheses, the pattern o prosthesis-engaging and supporting means is modified using the implant, tissue and adjacent structures in a patient's mouth as guides for the amount of bending and bulk removal.

In the indirect molding methods, the unmodified coping insert is placed in an implant, an impression is made of the affected area, and the insert is removed from the implant and placed into the negative opening in the impression. An appropriate replica of the top of the implant is placed on the protruding shaft of the insert, and a mixture of stone is poured into the impression to create a replica of the affected mouth area. The insert can then be modified outside the mouth, and the prosthesis can be cast in appropriate dental alloys such as gold. The modified prosthesis-engaging means can then be cemented into the implant in the patient's mouth, and a prosthesis joined to it.

The indirect method has several advantages. The patient spends less time in a dentist's office; the indirect method makes it easier to form a prosthesis of ideal size and shape than the direct method; and the insert and dental prosthesis can be formed during the healing period following insertion of the implant in the jaw of a patient, further shortening overall patient treatment time.

What is claimed is:

1. A coping insert made of thermoplastic material, and adapted for use with an endosseous dental implant anchoring means comprising a shaft means adapted for insertion into a passage in said endosseous dental implant anchoring means; abutment head means atop, and joined to said shaft means, said abutment head means being adapted to conform to the top surface of said endosseous dental implant anchoring means; restriction means atop and joined to said abutment head means, said restriction means comprising a region of reduced cross-section having a size and shape sufficient to facilitate perferential bending at said restriction means when said coping insert is heated to the softening temperature of the thermoplastic; and atop, and joined to said restriction means, means for engaging and supporting dental prosthesis means.

2. The insert of claim 1 wherein said shaft means includes at least one groove means for facilitating removal of the portion of the shaft means below said groove means by severing said shaft means through said groove means.

3. The insert of claim 1 further comprising means on said engaging/supporting means for facilitating severing, as desired, portions of said engaging/supporting means therefrom.

4. The insert of claim 1 wherein said restriction means comprises a circumferential groove having a rounded, concave profile.

5. A one-piece, thermoplastic coping insert adapted for use with an endosseous dental implant anchoring means comprising shaft means adapted for insertion into a passage in said endosseous dental implant anchoring means; abutment head means integrally joined to said shaft means, said abutment head means being adapted to conform to, and to abut the top surface of said endosseous dental implant anchoring means; means for engaging and supporting dental prosthesis means; and restriction means comprising a region of reduced cross-section linking the upper end of said abutment head means to the lower end of said engaging/supporting means, said restriction means being adapted to bend when said insert is heated to the softening temperature of the thermoplastic from which said insert is made without bending or distorting said abutment head means or said engaging/supporting means.

6. The insert of claim 5 wherein said shaft means includes at least one groove means for facilitating removal of the portion of the shaft means below said groove means by severing said shaft means through said groove means.

7. The insert of claim 5 further comprising means on said engaging/supporting means for facilitatng severing, as desired, portions of said engaging/supporting means therefrom.

8. The insert of claim 5 wherein said restriction means comprises a circumferential groove having a rounded, concave profile.

9. A coping insert made of thermoplastic material, and adapted for use with an endosseous dental implant anchoring means comprising shaft means adapted for insertion into a passage in said endosseous dental implant anchoring means; abutment head means atop, and joined to said shaft means, said abutment means being adapted to conform to the top surface of said endosseous dental implant anchoring means; and atop, and joined to said abutment head means, a means for engaging and supporting dental prosthesis means whereby said insert, when heated to the softening point of the thermoplastic material, can be bent as desired.

10. The insert of claim 9 wherein said shaft means has at least two portions of different diameter adapted to fit into a complementary passage in said endosseous dental implant anchoring means.

11. The insert of claim 1 wherein said shaft means has at least two portions of different diameter adapted to fit into a complementary passage in said endosseous dental implant anchoring means.

12. The insert of claim 5 wherein said shaft means has at least two portions of different diameter adapted to fit into a complementary passage in said endosseous dental implant anchoring means.

13. A coping insert made of thermoplastic material, and adapted for use with endosseous dental implant anchoring means comprising shaft means having at least two portions of different diameter adapted to fit into a complementary passage in said endosseous dental implant anchoring means; abutment head means atop, and joined to said shaft means, said abutment means being adapted to conform: to the top surface of said endosseous dental implant anchoring means, whereby said insert, when heated to the softening point of the termoplastic material, can be bent as desired.

* * * * *